US007939479B2

(12) United States Patent
Chandler

(10) Patent No.: US 7,939,479 B2
(45) Date of Patent: May 10, 2011

(54) DRY HAND CLEANER COMPRISING CORNCOB PARTICLES

(76) Inventor: Barry E. Chandler, Houston, TX (US)

( * ) Notice: Subject to any disclaimer, the term of this patent is extended or adjusted under 35 U.S.C. 154(b) by 437 days.

(21) Appl. No.: 12/075,496

(22) Filed: Mar. 12, 2008

(65) Prior Publication Data

US 2009/0233826 A1 Sep. 17, 2009

(51) Int. Cl.
*A61K 7/50* (2006.01)

(52) U.S. Cl. ........ 510/130; 510/137; 510/138; 510/139; 510/157; 510/473

(58) Field of Classification Search ........................ None
See application file for complete search history.

(56) References Cited

U.S. PATENT DOCUMENTS

| | | | |
|---|---|---|---|
| 3,956,197 | A | 5/1976 | Schoenholz et al. |
| 4,434,067 | A | 2/1984 | Malone et al. |
| 4,440,661 | A | 4/1984 | Takeuchi et al. |
| 4,648,882 | A | 3/1987 | Osberghaus et al. |
| 4,659,494 | A | 4/1987 | Soldanksi et al. |
| 5,268,400 | A | 12/1993 | Iseler et al. |
| 5,527,783 | A | 6/1996 | Derrien et al. |
| 6,092,302 | A | 7/2000 | Berrigan |
| 6,387,847 | B1 | 5/2002 | Yvin et al. |
| 6,419,962 | B1 | 7/2002 | Yokoyama et al. |
| 6,432,429 | B1 | 8/2002 | Maddern et al. |
| 6,528,047 | B2 | 3/2003 | Arif et al. |
| 6,583,097 | B2 | 6/2003 | McDonald |
| 6,625,612 | B1 | 9/2003 | Tal et al. |
| 6,635,612 | B1 | 10/2003 | Norman et al. |
| 6,884,763 | B2 | 4/2005 | Willard et al. |
| 6,955,817 | B2 | 10/2005 | McAtee et al. |
| 7,217,752 | B2 | 5/2007 | Schmucker-Castner et al. |
| 7,223,723 | B2 | 5/2007 | Wilson |
| 7,241,452 | B2 * | 7/2007 | Veeger et al. ................. 424/401 |
| 7,257,932 | B2 | 8/2007 | Ng |
| 7,262,159 | B2 | 8/2007 | Nguyen et al. |
| 7,300,957 | B1 | 11/2007 | Whewell |
| 7,316,201 | B2 | 1/2008 | Rasner et al. |
| 2003/0125223 | A1 | 7/2003 | Denton |

OTHER PUBLICATIONS www.bepex.com/schugi.htm.
www.sigmaaldrich.com/SAFC/Global/bOverviewb.html.
www.meangreen.com/pages/handcleaners.htm.

* cited by examiner

*Primary Examiner* — Necholus Ogden, Jr.
(74) *Attorney, Agent, or Firm* — Browning Bushman P.C.

(57) ABSTRACT

A lightweight, flowable, dry powder plant-based absorbent hand cleaner and method of manufacturing the hand cleaner are disclosed. The composition may include ground corn cobs particles of a selected size, one or more lathering surfactants, and one or more conditioning components. The composition may be mixed into a slurry and dried by a non-spray drying process. The user's hands may be scrubbed together, forming an abrasive agglomeration which removes/absorbs and absorbs the dirt, oil, grease and other foreign material from the hands, then the hands are rinsed with water.

21 Claims, 1 Drawing Sheet

DRY HAND CLEANER COMPRISING CORNCOB PARTICLES

FIELD OF THE INVENTION

The present invention relates to a dry cleaner and, more particularly, relates to a dry hand cleaner which may be easily dispersed and applied to the wetted hands of the user to clean the hands. The dry hand cleaner comprises a dry base of cellulose particles, such as corncob particles, and surfactants and conditioners which are mixed with the cellulose particles to form a slurry then dried.

BACKGROUND OF THE INVENTION

Numerous types of cleaners have been devised, and most cleaners designed for cleaning hands are in a liquid or paste form. Liquid and paste cleaners are relatively heavy and thus expensive to ship, particularly compared to cellulose materials which provide both a scrubbing and absorbent action. Cellulose particles alone, however, do a poor job of cleaning grease and dirt from the hands, and surfactants in dry form which may be added to the cellulose particles do not tend to maintain a uniform consistency. Lighter cellulose particles may thus rise to the top of a container during shipment, while the heavier dry surfactants tend to drop toward the bottom of the container.

U.S. Pat. No. 5,527,783 discloses a solid composition based on plants, wherein the plant particles are immersed in a solvent, and a liquid phase and solid phase are separated. This slurry is dried until about 90% of the aqueous solvents are removed, then a surfactant type absorption promoter is added with a suitable amount of liquid to form a paste. The paste is finally converted to a porous form by freezing and sublimation. U.S. Pat. No. 4,659,494 discloses a carpet cleaning composition which comprises an absorbent, water, and an organic solvent. The composition is substantially dry, but is also slightly moist.

Various dry and paste type cleaners have been devised. U.S. Pat. No. 6,092,302 discloses a wood pulp composition suitable for cleaning a floor. A fluid bed drier heats the pulp to temperatures up to 800° F. U.S. Pat. No. 6,387,847 discloses an aqueous cleaning solution which is also available in powder form. Clay is used as the base, and the composition has a pH of 2 or less. U.S. Pat. No. 6,419,962 discloses a skin treatment composition which utilizes plant materials. U.S. Pat. No. 6,528,047 discloses a home care concentrate with odor absorption and deodorization properties. U.S. Pat. No. 6,583,097 discloses a cleaner containing various oils and degreasers. U.S. Pat. No. 6,625,612 discloses a detergent composition with increased flowability. U.S. Pat. No. 7,217,752 discloses an aqueous surfactant composition. U.S. Pat. No. 7,223,723 discloses a liquid cleaning composition. U.S. Pat. No. 7,241,452 discloses a skin and hair care agent, and U.S. Pat. No. 7,300,957 discloses a skin care composition.

U.S. Pat. No. 3,956,197 discloses a dry powder cleaner with a water immiscible organic liquid of at least 1% by weight. U.S. Pat. No. 4,434,067 discloses a powdered cleaning composition containing a urea-formaldehyde polymeric material. A powder cleaning composition with organic fibers, a resin, surfactant, and water are disclosed in U.S. Pat. Nos. 4,440,661, 4,648,882 discloses a carpet cleaning composition containing surfactants, solvents, and zeolite. A flowable powder fabric dry cleaning formula is disclosed in U.S. Pat. Nos. 5,268,400, 6,432,429 discloses a hand cleaning formulation with absorbing substrate, esters, surfactants, and water. Publication 2003/0125223 discloses a hand cleaning composition with various solvents and water.

The disadvantages of the prior art are overcome by the present invention, and an improved dry cleaner, particularly suitable for hand cleaning, is hereinafter disclosed.

SUMMARY OF THE INVENTION

In one embodiment, a dry hand cleaner includes a dry base of cellulose particles, one or more dried surfactants, and one or more dried conditioners. The surfactants and the conditioners are coated on an exterior surface of the cellulose particles.

In a preferred embodiment, the one or more conditioners and the one or more surfactants are combined with the cellulose particles to form a slurry mixture which is dried to form dry cellulose particles coated on an exterior surface with the one or more surfactants and the one or more conditioners.

These and further features and advantages of the present invention will become apparent from the following detailed description, wherein reference is made to the figures in the accompanying drawings.

DETAILED DESCRIPTION OF PREFERRED EMBODIMENTS

Figure 1:
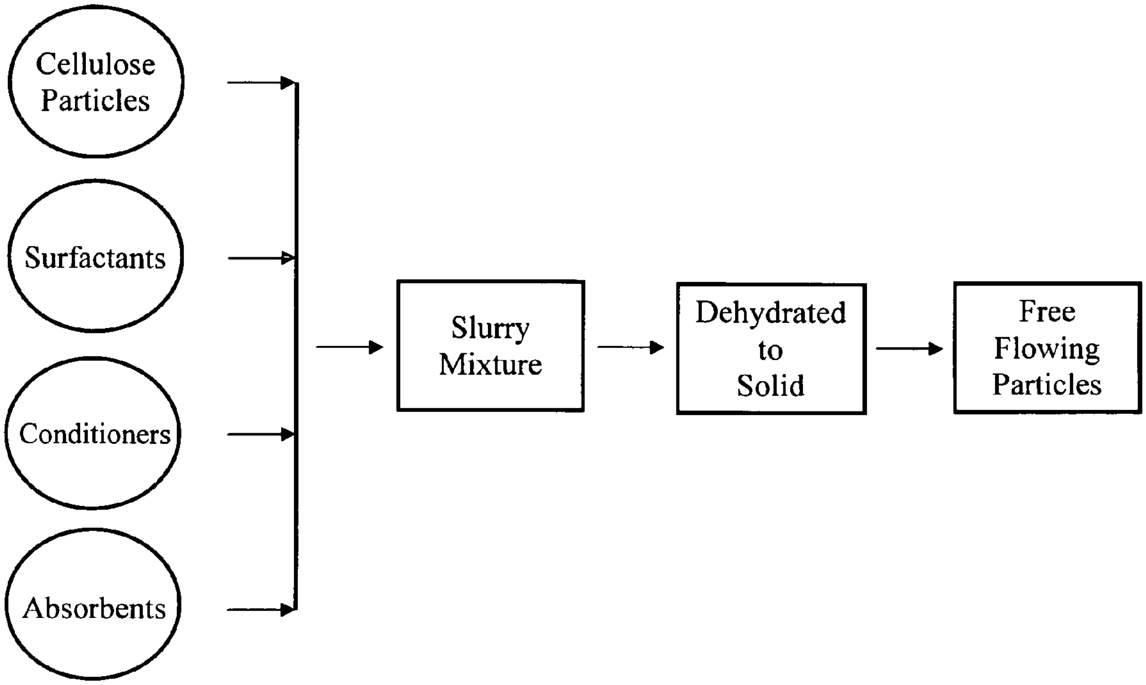
FIG. 1 is a diagram of the process for forming a dry hand cleaner.

FIG. 1 generally illustrates the process for forming a free flowing hand cleaner. The invention utilizes cellulose particles 12, and preferably corncob particles which are lightweight, absorbent, and act as a mild abrasive during the hand cleaning operation. Suitable corncob particles are of a type wherein the majority of the particles have a mean diameter of from 100 microns to 300 microns.

The hand cleaner also includes one or more surfactants 14. Suitable surfactants may be of a solid, liquid, or gel form before being mixed with other ingredients, e.g., by a tumbling drum. Suitable surfactants may be used from a list including ammonium laureth sulfate, tetrasodium EDTA, triethanolamine, nonyl phenoxypolyethanoxy ethanol, cocodiethanolamide. All of these surfactants may be used at a rate of from 1 to 10% of total weight of the cleaner.

The dry hand cleaner also includes conditioners 16. Various conditioners may provide pH regulation or provide oils which are conducive to maintaining the hands in a good condition. Suitable conditioners include petrolatum, mineral oil, lanolin, DMDM hydantoin, basil oil, almond oil, soy oil, glycerin, lanolin, wheat germ extract and vitamins A, C and E, aloe. All of these skin conditioners may be used at a rate of from 0.05 to 1% of the total weight of the cleaner.

The hand cleaner may also include one or more additional absorbents 18, such as zeolite or bentonite. Zeolite is particularly desirable since it acts as both an absorbent and promotes free flowing of the dry hand cleaner. Additional materials in small amounts may also be added to the mixture.

The above ingredients are then combined and mixed to form a slurry 20. After being thoroughly mixed, the slurry is dehydrated or dried to form a solid. A suitable dryer may inject the mixture via spray nozzles, and avoids the material buildup from using fine powders. The preferred drying temperature is between 150° and 280°, and more particularly from 180° F. to 220° F. A relatively low drying temperature is used so that the corncob particles don't "burn", to reduce the amount of conditioners which volatize rather than being coated on the surface of the cellulose particles, and to reduce energy losses. The following table sets forth the various materials that are included in the slurry, and the preferred amount for the materials.

| Material | Amount | Preferred Amount |
|---|---|---|
| Cellulose particles | At least 40-60% by volume | At least 60-70% by volume |
| Surfactants | 5-20% by weight | 5-15% by weight |
| Conditioners | Less than 3% by weight | Less than 2% by weight |
| Absorbents | Less than 3% by weight | Less than 2% by weight |

As indicated above, various types of conditioners may be used, and the selected amount of each conditioner will depend to some extent on other conditioners. Aloe is a preferred conditioner, and may be included in an amount of less than 1% by weight. Both zeolite and bentonite are preferred absorbers, and zeolite may be used at a rate of less than 1% by weight for both absorption and free flowing of the hand cleaner. If bentonite is added as an absorption material, it preferably is less than 2% by weight.

Figure 2:
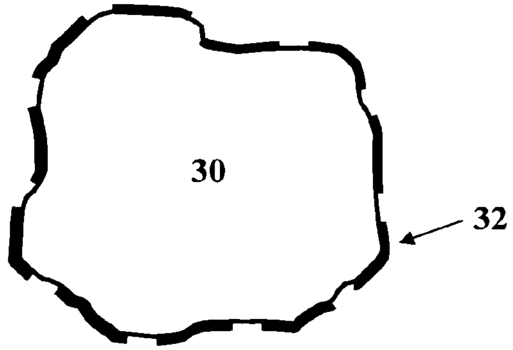
FIG. 2 illustrates an enlarged view of a cellulose particle coated with the surfactant and the conditioner.

FIG. 2 conceptually illustrates a cellulose particle 30 with a coating 32 which contains one or more surfactants and one or more conditioners from the mixture. This coating is attached to the particles in a fairly strong manner since the drying process effectively bonds the surfactants and conditioners to the outside of the cellulose particles. Substantially the entirety of the exterior of the cellulose particle preferably is coated with the mixture, as shown in FIG. 2. Also, the liquid mixture penetrates all or a substantial portion of the core of each cellulose particle, with water being absorbed by the absorbent cellulose material.

Corncobs are particularly suitable as a cellulose material because they are relatively inexpensive, and are lightweight. Since the bulk of the product is formed from these particles, the product may be shipped at a lower cost than liquid or gel cleaners, and may be easily stored and handled. Commonly used liquid and paste hand cleaners have a density which approximates water. The density of conventional liquid and paste hand cleaners varies from about 61 lb/ft$^3$ to about 65 lb/ft$^3$. A commonly used hand cleaner Baraxo™ is somewhat lighter, but still has a density of about 49 lb/ft$^3$. According to the present invention, cellulose material hand cleaner may have a density from about 20 lb/ft$^3$ to about 30 lb/ft$^3$, and many in applications from about 20 lb/ft$^3$ to 26 lb/ft$^3$. Embodiments manufactured to date from a corncob cellulose material with the surfactants and conditioners as disclosed herein have a density of from about 22 lb/ft$^3$ to about 24 lb/ft$^3$.

While other cellulose materials might be used, corncobs are particularly well suited for the present application because of their light weight, which is primarily due to the porous nature of the particles, and because of their mild abrasiveness which facilitates hand cleaning. It is thus the combination of the light weight and the abrasive nature of the corncob particles which make this material particularly well suited for a hand cleaner.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A dry hand cleaner, comprising:
a dry base of cellulose particles including corncob particles;
one or more dried surfactants; and
one or more dried conditioners, the one or more surfactants and the one or more conditioners coated on exterior surfaces of the cellulose particles.

2. A dry hand cleaner as defined in claim 1, wherein the base of cellulose particles comprises at least 80% by volume of the dry hand cleaner.

3. A dry hand cleaner as defined in claim 1, wherein the one or more surfactants comprise from 5-15% by weight of the dry hand cleaner.

4. A dry hand cleaner as defined in claim 1, wherein the one or more conditioners comprise less than 2% by weight of the dry hand cleaner.

5. A dry hand cleaner as defined in claim 1, wherein the dry hand cleaner has a density of from 22 lb/ft$^3$ to 26 lb/ft$^3$.

6. A dry hand cleaner as defined in claim 1, further comprising:
less than 1% by weight zeolite for free flowing of the dry hand cleaner.

7. A dry hand cleaner as defined in claim 1, further comprising:
less than 2% by weight bentonite.

8. A dry hand cleaner as defined in claim 1, wherein a majority of the corncob particles have a mean diameter of from 100 microns to 300 microns.

9. A dry hand cleaner, comprising:
a dry base of cellulose particles comprising at least 80% by volume of the dry hand cleaner;
one or more dried surfactants; and
one or more dried conditioners, wherein the cellulose particles, the one or more surfactants, and the one or more conditioners are combined to form a slurry mixture which is dried to form dry cellulose particles coated on exterior surfaces with the one or more surfactants and the one or more conditioners.

10. A dry hand cleaner as defined in claim 9, wherein the cellulose particles include corncob particles.

11. A dry hand cleaner as defined in claim 10, wherein a majority of the corncob particles have a mean diameter of from 100 microns to 300 microns.

12. A dry hand cleaner as defined in claim 9, wherein the one or more surfactants comprise from 5-15% by weight of the dry hand cleaner and the one or more conditioners comprise less than 2% by weight of the dry hand cleaner.

13. A dry hand cleaner as defined in claim 9, wherein the dry hand clean has a density of from 22 lb/ft$^3$ to 26 lb/ft$^3$.

14. A method of forming a dry hand cleaner, comprising:
combining a dry base of cellulose particles including corncob particles having a mean diameter of 100 microns to 300 microns with one or more surfactants and one or more liquid conditioners to form a slurry mixture; and
drying the slurry mixture to remove moisture and form the dry hand cleaner with corncob particles coated with the one or more surfactants and the one or more conditioners.

15. A method as defined in claim 14, wherein the slurry mixture is dried from 180° F. to 220° F.

16. A method as defined in claim 14, wherein the surfactants comprise from 5-15% by weight of the hand cleaner, and the one or more conditioners comprise less than 2% by weight of the dry hand cleaner.

17. A method as defined in claim 14, wherein the dry hand cleaner has a density of from 22 $lb/ft^3$ to 26 $lb/ft^3$.

18. A dry hand cleaner, comprising:

a dry base of cellulose particles including corncob particles having a mean diameter of from 100 microns to 300 microns;

one or more dried surfactants; and one or more dried conditioners.

19. A dry hand cleaner as defined in claim 18, wherein the corncob particles comprise at least 80% by volume of the dry hand cleaner.

20. A dry hand cleaner as defined in claim 18, wherein the one or more surfactants comprise from 5-15% by weight of the dry hand cleaner and the one or more conditioners comprise less than 2% by weight of the dry hand cleaner.

21. A dry hand cleaner as defined in claim 18, wherein the dry hand cleaner has a density of from 22 $lb/ft^3$ to 26 $lb/ft^3$.

* * * * *